United States Patent [19]

Hudrlik

[11] Patent Number: 5,233,985
[45] Date of Patent: Aug. 10, 1993

[54] CARDIAC PACEMAKER WITH OPERATIONAL AMPLIFIER OUTPUT CIRCUIT

[75] Inventor: Terrence R. Hudrlik, Fridley, Minn.

[73] Assignee: Medtronic, Inc., Minneapolis, Minn.

[21] Appl. No.: 730,160

[22] Filed: Jul. 15, 1991

Related U.S. Application Data

[63] Continuation-in-part of Ser. No. 566,636, Oct. 10, 1990, abandoned, and a continuation-in-part of Ser. No. 827,858, Jan. 30, 1992, Pat. No. 5,156,149, and a continuation-in-part of Ser. No. 626,061, Dec. 12, 1990.

[51] Int. Cl.⁵ .......................................... A61N 1/362
[52] U.S. Cl. ...................................................... 607/27
[58] Field of Search ........................................ 128/419

[56] References Cited

U.S. PATENT DOCUMENTS

| | | | |
|---|---|---|---|
| 3,057,356 | 10/1962 | Greatbatch | 128/419 PG |
| 3,835,865 | 9/1974 | Bowers | 128/419 PG |
| 4,114,627 | 9/1978 | Lewyn et al. | 128/419 PG |
| 4,170,999 | 10/1979 | Allen et al. | 128/419.2 PG |
| 4,261,365 | 4/1981 | Nordling | 128/419 PG |
| 4,289,134 | 9/1981 | Bernstein | 128/419 PG |
| 4,305,396 | 12/1981 | Kampf et al. | 128/419 PG |
| 4,399,818 | 8/1983 | Mongy | 128/419 PG |
| 4,406,286 | 9/1983 | Skin | 128/419 PG |
| 4,476,868 | 10/1984 | Thompson | 128/419 PG |
| 4,498,478 | 2/1985 | Bourgeois | 128/419.2 PG |
| 4,532,931 | 8/1985 | Miles | 128/419 PG |
| 4,729,376 | 3/1988 | DeCote, Jr. | 128/419 PT |
| 4,759,366 | 7/1988 | Callaghan | 128/419 PG |
| 4,768,511 | 9/1988 | Decote, Jr. | 128/419 PG |
| 4,811,738 | 3/1989 | Economides et al. | 128/419.2 PG |
| 4,858,610 | 8/1989 | Callaghan et al. | 128/419 PG |
| 4,878,497 | 11/1989 | Callaghan et al. | 128/419 PG |

*Primary Examiner*—William E. Kamm
*Attorney, Agent, or Firm*—Reed A. Duthler; Harold R. Patton

[57] ABSTRACT

A medical electrical stimulator employing an operational amplifier output circuit for producing an electrical stimulating pulse for application to body tissue and for sensing electrical activity in the body tissue. A first input to the operational amplifier is coupled through a virtual load to a probe electrode in close proximity to the body tissue. The second input is coupled to a second electrode which may be remote from the tissue to be stimulated. A defined voltage signal may be provided to the second input to the amplifier, and the amplifier correspondingly delivers current through the virtual load to the probe electrode as the amplifier maintains equal voltage levels at its two inputs. The current delivered to the probe electrode functions to stimulate the body tissue. By varying the defined voltage signals provided to the second input of the amplifier, arbitrary stimulation pulse waveforms may be generated. After termination of the defined voltage signal, the amplifier functions to restore the electrode-tissue system to its previous electrical equilibrium condition and to sense induced or spontaneous electrical activity in the tissue. The circuit may be employed in cardiac pacemakers, with the probe electrode located on or in the heart, or in other electrical medical stimulators.

12 Claims, 6 Drawing Sheets

CARDIAC PACEMAKER WITH OPERATIONAL AMPLIFIER OUTPUT CIRCUIT

CROSS REFERENCE TO RELATED APPLICATIONS

Attention is drawn to the commonly assigned co-pending U.S. Patent Application Ser. No. 07/566,636, for a "Field Density Clamp for sensing Cardiac Depolarizations", filed Oct. 8, 1990 in the name of Terrence R. Hudrlik now abandoned and replaced by U.S. patent application Ser. No. 07/827,858, filed Jan. 30, 1992, issued as U.S. Pat. No. 5,156,149 and U.S. patent application Ser. No. 07/626,061, "Electronic Capture Detection for a Pacer", filed Dec. 12, 1990 in the name of Terrence R. Hudrlik, both of which are incorporated herein in by reference in their entireties. The present application is a continuation in part of both of these cited applications.

BACKGROUND OF THE INVENTION

This invention relates to electrical tissue stimulators and more particularly, to tissue stimulator output circuits and sense amplifier circuits.

Electrical body tissue stimulators, such as nerve or muscle stimulators, cardiac pacemakers and the like are well known in the prior art. Electrical energy has been applied to body tissue using batteries, condensers, electrostatic charge generators and alternating current generators either for scientific curiosity or for treatment of various injuries and illnesses. Condenser discharge impulses of electrical energy into body tissue have been used therapeutically since the invention of the Leyden jar and their use continues today in implantable body stimulators, particularly cardiac pacemakers.

Early implantable cardiac pacemakers, such as those shown in U.S. Pat. No. 3,057,356 and subsequent pacemakers up to the present date comprise small, completely implantable, transistorized and battery operated pulse generators connected to flexible leads bearing electrodes directly in contact with cardiac tissue. Demand cardiac pacemakers have traditionally employed a timing circuit, a stimulating circuit and a separate sensing circuit, all of which draw current from the power source. The stimulating circuits of such pulse generators have traditionally comprised constant current or constant voltage output circuits employing output capacitors which are charged to battery potential through a relatively high impedance and discharged through electrodes in contact with myocardial tissue to stimulate depolarization of the tissue. The output capacitors are typically recharged during the intervals between successive discharges.

The discharge of an output capacitor through the myocardial tissue results in after-effects due to the disruption of the electrical equilibrium condition at the tissue-electrode interface and the polarization of the tissue's intrinsic dipole moments. Post relaxation of these stimulation based after-effects, traditionally characterized as "polarization", manifest themselves to traditional pacemaker sense amplifiers coupled to the stimulation electrode as voltage signals which persist for a period of time following delivery of stimulation pulses. In traditional pacemakers, these after-effects interfere with the pacemaker's ability to sense depolarizations of the heart during, closely following or caused by delivery of stimulation pulses.

Various attempts were made in the prior art to counteract the "polarization" after-effects of the stimulation pulse and simultaneously recharge the output capacitor by means of a fast recharge pulse delivered through the stimulation electrodes following the trailing edge of the output pulse, as exemplified by U.S. Pat. Nos. 4,476,868, 4,406,286, 3,835,865 and 4,170,999. However, simply passing sufficient current through the electrode-tissue interface to recharge the output capacitor does not necessarily return the electrode-tissue system to its prior electrical equilibrium condition. Alternatively, it has been suggested to counteract the after-effects of delivery of a stimulation pulse by simply tying the electrodes involved in delivery of the pulse together following delivery of the pulse, as disclosed in U.S. Pat. No. 4,498,478 issued to Bourgeois or by means of a train of low energy pulses as disclosed in U.S. Pat. No. 4,811,738, issued to Economides, et al.

SUMMARY OF THE INVENTION

The method and apparatus of the present invention contemplates the use of the field density clamp operational amplifier both to effect body tissue stimulation and to sense electrical activity in the body tissue. Therefore it is an object of the present invention to provide a stimulating pulse output circuit which is capable of stimulating body tissue, particularly myocardial tissue, sufficient to effect a desired tissue response, such as depolarization, while reducing post pulse disturbances of the electrode/tissue equilibrium condition normally present between stimulation pulses and/or tissue depolarizations.

It is a further object of the present invention to provide a simplified stimulation pulse generator which eliminates the output capacitor and avoids the complexity of circuit components which have been provided to correct for or compensate for "polarization" effects in the prior art. Elimination of the traditional output capacitor provides an additional substantial benefit in that arbitrary output waveforms may be defined an applied to the exitable tissue simply by varying the defined controlling voltage signal. Extended pulse waveforms, ramped voltage waveforms, and constant voltage waveforms, for example, may all readily be accomplished. Both suprathreshold and subthreshold pulses may be generated and delivered.

The ready adjustability of the stimulation pulse waveform in conjunction with the ability to sense tissue depolarizations closely following delivery of the stimulation pulse also provide a sensing and stimulating system which is beneficially used in a pacemaker as 07/626,061, by Hudrlik. This application also discloses a pacemaker which monitors the success of the stimulation pulses in capturing the heart tissue and adjusts the stimulation pulse energy accordingly.

It is still further an object of the present invention to eliminate or reduce the necessity for providing blanking and refractory intervals during and following the delivery of a stimulating output pulse, particularly in the context of single and dual chamber cardiac pacing systems.

It is still a further object of the present invention to employ the amplifier as both the sense amplifier for sensing natural depolarizations of the heart and as the output pulse generator of a body tissue stimulator, such as a cardiac pacemaker.

These and other objects of the present invention are realized in the output pulse stimulating circuit of the present invention which comprises an operational amplifier having first and second input terminals and an output terminal, a feedback resistor coupled between the first input terminal and the output terminal of the operational amplifier, a first, probe electrode adapted to be placed in contact with tissue to be stimulated and coupled by a first lead to the first (negative) input terminal of the operational amplifier through a virtual load resistance, a second electrode adapted to be coupled to body tissue and coupled to the second (positive) input terminal of the operational amplifier, and a source for a defined voltage signal which may be applied to the second input to the amplifier. The defined voltage signal, when applied to the second input of the amplifier, forces the first input of the amplifier to the defined voltage. The first input to the amplifier is forced to the defined voltage by means of current applied through the feedback and virtual load resistor. This feedback process reproduces and maintains the defined voltage at the first (negative) input of the operational amplifier and this voltage, as applied to the probe electrode comprises the stimulation pulse.

In the context of the present invention, the virtual load impedance may be chosen to provide a low input impedance to the amplifier, for example 100 ohms or less. The virtual load impedance and the capacitive and resistive characteristics of the tissue-electrode system, define the current provided to the probe electrode as a function of the defined voltage signal.

The virtual load impedance may be adjusted to vary the sensing characteristics of the amplifier as disclosed in the above cited application Ser. No. 07/566,636. The stimulation pulse characteristics may be varied by adjusting the defined voltage signal provided to the second input of the amplifies and by adjustment of the virtual load and feedback impedances. By adjusting these parameters, a wide variety of sensing and stimulation characteristics can easily be obtained, and the device may be optimized for use with electrodes of varying types.

BRIEF DESCRIPTION OF THE DRAWINGS

The above and still further objects, features and advantages of the present invention will become apparent from the following detailed description of a presently preferred embodiments, taken in conjunction with the accompanying drawings, and, in which.

DETAILED DESCRIPTION OF THE PREFERRED EMBODIMENT

In the following description, reference is made to illustrative embodiments for carrying out the invention. It is understood that other embodiments may be utilized without departing from the scope of the invention. For example, the invention is disclosed in the context of a VVI single chamber pacemaker system for treating bradycardia. It should be appreciated that the technique for myocardial depolarization stimulation and detection could also be applied to other forms of pacemakers and heart stimulators including dual chamber pacemakers (DDD, VDD, DVI, etc), rate responsive pacemakers (single and dual chamber) and antitachyarrhythmia devices. The detection of signals from and/or the stimulation of other body tissue than myocardial tissue may also be accomplished using the present invention. For example, the concepts of the present invention may be employed in electrical stimulation systems for stimulating other organ and skeletal muscle systems and/or the nervous system of a patient.

Figure 1:
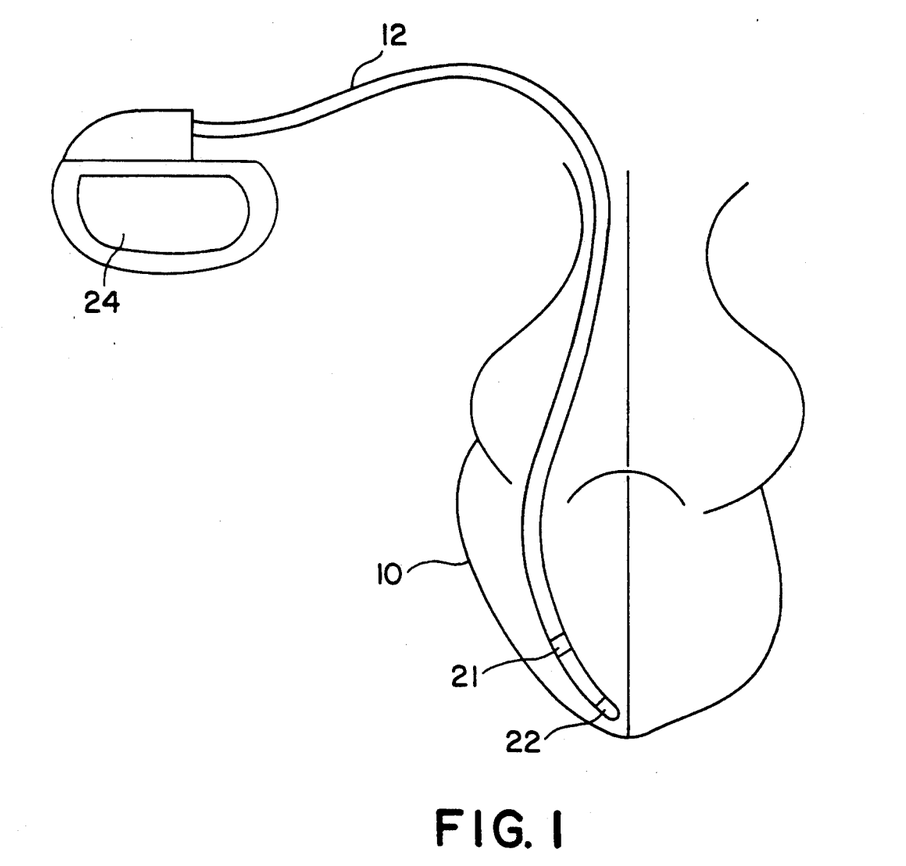
FIG. 1 is a schematic diagram depicting the interconnection of a pacemaker pulse generator and pacing lead with the heart.

FIG. 1 is a representation of an implanted pacemaker 14 in relation to a lead system 12 and heart 10. Typically, the pacemaker 14 is implanted beneath the patient's skin, outside the rib cage in the pectoral region. A pacing lead 12 is passed pervenously through the right atrium and into the right ventricle of the heart 10. The pacing lead 12 is used for supplying pacing pulses to the heart and conducting electrical signals resulting from depolarizations of the heart tissue to the pacemaker 14.

Figure 2:
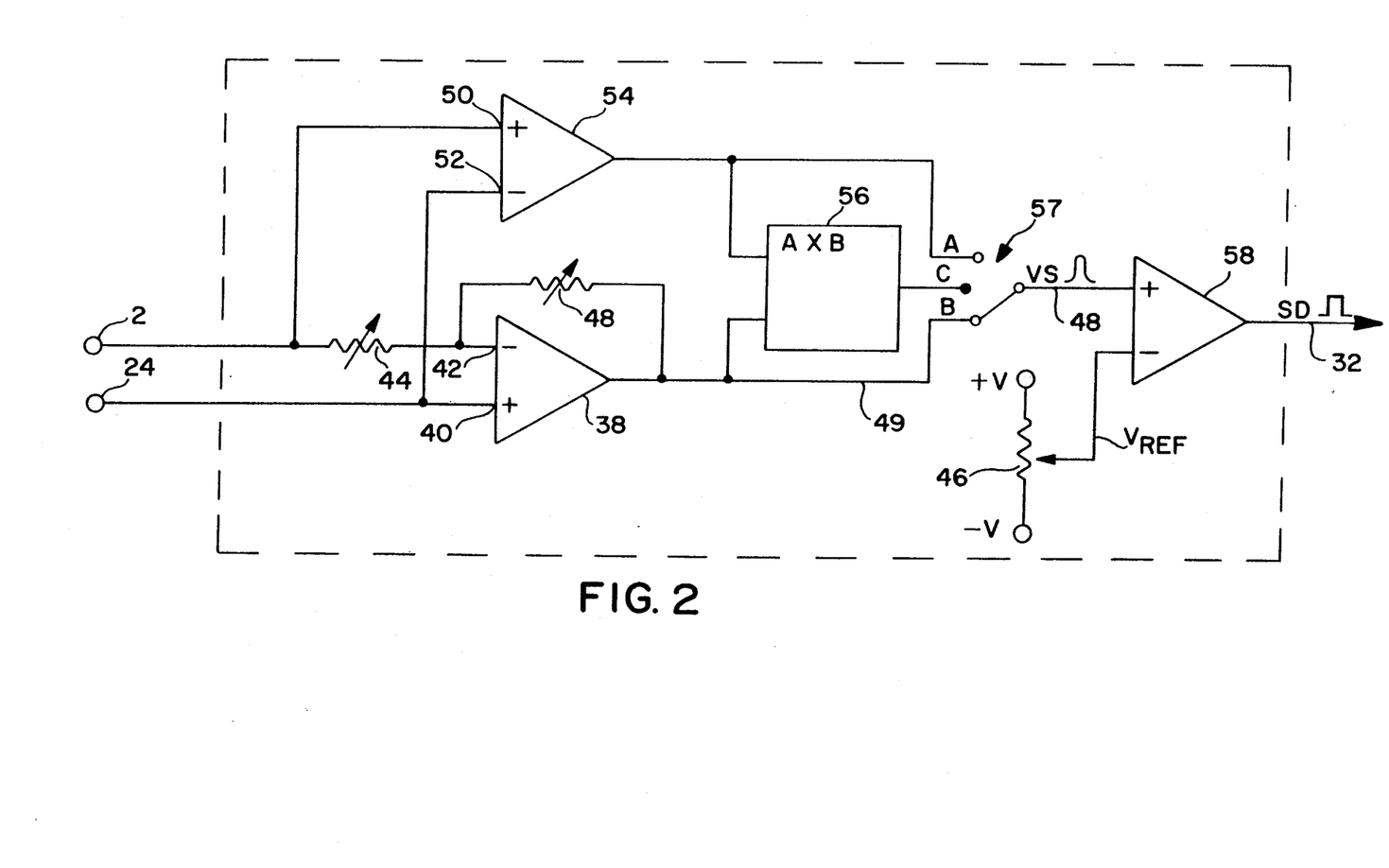
FIG. 2 is a schematic diagram illustrating a field density clamp amplifier configured for use as a sense amplifier only.

There are two basic sensing configurations which may be employed using pacing lead 12. A unipolar electrode configuration would employ tip electrode 22, referenced to case electrode 24. Typically the distance between the distal tip electrode 22 and the pacer case electrode 24 is between 10 and 30 cm. A bipolar electrode configuration would employ ring electrode 21 and tip electrode 22. Typically, the tip and ring electrodes 22 and 21 are spaced apart between 0.5 and 3.0 cm. In dual chamber pacemakers, electrodes for unipolar and/or bipolar sensing are similarly situated on or in the atrium or coronary sinus. FIG. 2 discloses an amplifier for use in conjunction with the present invention. This form of amplifier is also described in the above-cited co-pending patent applications by Hudrlik, incorporated by reference in their entirety. The active circuitry of the amplifier 38 attempts to maintain equal voltage levels at its two inputs. Passage of a depolarization wavefront changes the distribution of electrical charges and the electric field in the vicinity of the electrode 22. This disturbance results in the active circuitry of the amplifier delivering current through feedback resistor 48 and virtual load resistor 44 to maintain equal voltages at its inputs. This current, delivered to electrode 22, serves both to reestablish the equilibrium condition in effect preceding the passage of the depolarization wavefront and to signal the occurrence of the depolarization wavefront.

As shown in the schematic diagram of FIG. 2, the sense amplifier may be practiced with an operational amplifier 38 which has its non-inverting input 40 connected to the can electrode 24. The inverting input 42 is coupled to tip electrode 22 through a variable resistor 44 which is used to set a virtual load resistance for the system. This resistance is preferably between 10 and 1000 ohms, and is preferably less than 100 ohms for use in conjunction with small surface area electrodes, typically about 5 square millimeters or less in surface area.

The inventor has determined that when an amplifier according to the present invention is coupled to a canine heart by means of a polished platinum probe electrode, R-waves exhibited during normal sinus rhythm place a peak demand for current through the virtual load of about 0.5 microamps per square millimeter of electrode surface. It is preferred that the peak current demand fall in the vicinity of 2.5 microamps or less, which can be accomplished with a platinum electrodes of about 2-5 square millimeters in surface area. Electrodes fabricated of other metals will have differing current requirements and therefore will have differing optimal size ranges. Electrodes directly in contact with the myocardium will typically require a greater peak current per square millimeter of surface area and therefore will typically have somewhat smaller optimal surface areas or will employ current shunts to redirect the excess current.

A feedback path is provided for the amplifier 38 by a feedback resistor 48 which defines a voltage signal B on line 39 proportional to the current through the virtual load 44 and feedback resistor 48. A differential amplifier 54 may optionally be provided to measure the magnitude of the potential difference between electrodes 22 and 25, and thus the voltage across the virtual load 44. The non-inverting input 50 of this differential amplifier 54 is coupled to tip electrode 22 while the can electrode 24 is coupled to inverting input 52. The voltage output A of differential amplifier 54 is proportional to the voltage across the virtual load resistor 44.

The voltage measurement A and the current measurement B may be used to compute the power delivered through the virtual load as a result of the passage of a cardiac depolarization wavefront. Detection of the passage of the depolarization wavefront based on measured power delivered through the virtual load may be employed for sensing purposes in the context of the present invention. However it is also workable to use the current signal B, alone, to detect the depolarization, and in the specific embodiments discussed below, only this signal is employed.

The power computation is carried out by an analog multiplier 56 which computes the power level an provides a voltage output C proportional to the computed power. Current signal B or power signal C is communicated to comparator 58 via switch 57. Comparator 58 compares the selected input to a threshold voltage VREF defined by voltage source 46. If the selected one of the current signal B or the power signal C exceeds Vref, comparator 8 generates a V-sense detect signal VSD on line 32.

Figure 3:
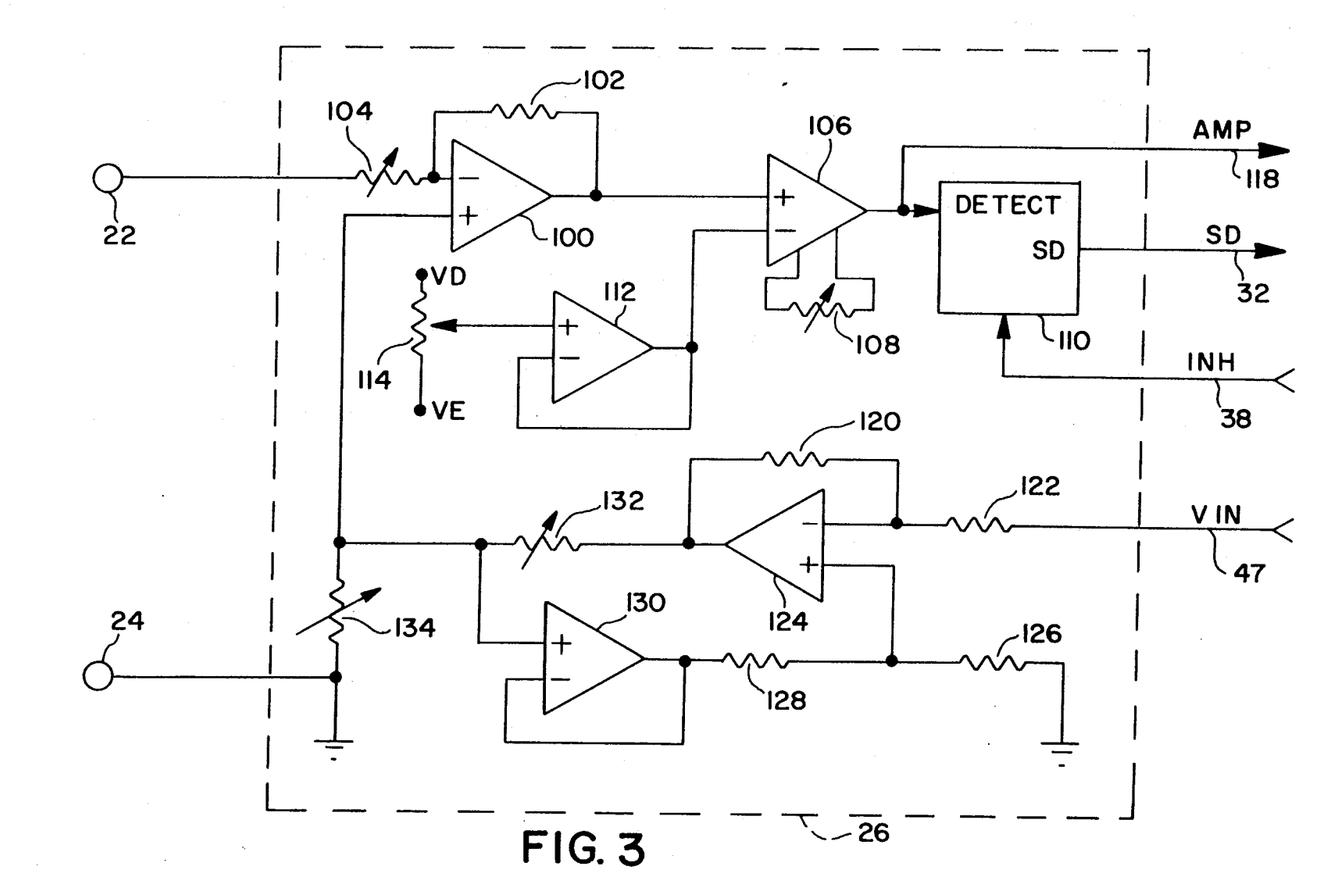
FIG. 3 is a schematic diagram depicting a first embodiment of the present invention in which the amplifier of the present invention is used as both a sense amplifier and the output circuitry for a cardiac pacemaker system.

FIG. 3 is a schematic diagram illustrating one embodiment of a combined input/output stage employing the field density clamp amplifier illustrated in FIG. 2. Operational amplifier 100 has its negative input coupled to probe electrode 22, through virtual load resistor 104. Load resistor 104 is shown as an adjustable resistor, an adjustment of load resistor 104 allows for tuning of the sense amplifier, as discussed in the above-cited Hudrlik application, Ser. No. 07/566,636. By reducing the application impedance of virtual load 104, the signal contribution of the heart tissue remote from electrode 22 is diminished, and the relative contribution of tissue in the immediate vicinity of electrode 204 is increased. For purposes of the present invention, a virtual load impedance of 100 ohms or less is believed to be preferable, with the virtual load impedance 104 as close to zero as is practicable. Indifferent electrode 24, which may take the form of all or a portion of the can of the pacemaker is coupled to the positive input of operational amplifier 00 through an adjustable resistor 134. Feedback resistor 102 defines a voltage at the output of amplifier 00 proportional to the current delivered through virtual load resistor 104. Operation of amplifier 100 to sense cardiac depolarizations corresponds to the operation of amplifier 38, discussed above in FIG. 2, and discussed extensively in the above-cited Hudrlik applications.

The output of amplifier 100 is coupled to the input of differential amplifier 106, which operates as an adjustable gain stage of conventional design, with gain being controlled by variable resistor 108. Operational amplifier 112 controls the offset of amplifier 106, which may be adjusted by means of a variable voltage provided by variable resistor 114. The output of amplifier 106 is provided to an amplifier output line 118, for use as an analog signal, if desired. The output of amplifier 106 is also provided to detection block 116, which detects the occurrence of a signal from amplifier 106 that exceeds a predetermined sensing threshold value. This threshold value may be a simple voltage level threshold or may be the composite output from a convolution based threshold detector.

Detection block 116 may correspond to circuitry used to establish sensing thresholds in any prior art pacemaker, and is illustrated functionally herein for that reason. In response to the output signal from amplifier 106 exceeding a predetermined threshold, positive or negative, a sense detect signal (SD) is generated on line 32. In order to prevent sense detect signals from being generated in response to delivery of the pacing pulse itself, the detection block may be inhibited during the pacing pulse and for the next few milliseconds thereafter by means of a signal on INH line 38. If the amplifier is not being used to perform capture detection as discussed below, the signal on INH line 38 may persist for up to 100 milliseconds after the pacing pulse, corresponding to the digital blanking intervals used on many prior art pacers. Alternatively, if amplifier 26 is being used to perform capture detection, the signal on INH line 38 may persist only long enough to allow the amplifier 100 to restore the equilibrium condition at the electrodes, e.g for about 5 ms.

Use of operational amplifier 100 to deliver a stimulation pulse is accomplished by imposing a predefined voltage at the positive input of amplifier 100, as discussed above. Operational amplifiers 124 and 130 in conjunction with associated resistors 120, 122, 126, 128 and 132 function to provide an adjustable, controlled current through resistor 134 as a function of the voltage applied to the negative input of amplifier 124 on line 47, marked "VIN". The current through resistor 134 is defines a voltage signal provided to the positive input of operational amplifier 100, triggering current flow through feedback resistor 102 which drives the inverting input of operational amplifier 102 to the same voltage as applied to the non-inverting input. This virtual node voltage (the voltage at the inverting input to amplifier 102) is applied across virtual load resistor 104 and probe electrode 22 to stimulate the heart.

Adjustment of the voltage signal provided to amplifier 100 may be accomplished by means of adjustment of resistor 132, resistor 134, or by variation of the signal provided via VIN line 47. Generally, the output 5 circuitry illustrated in this figure responds to a voltage on VIN line 47 by producing a current through virtual load resistor 104 sufficient to maintain the inputs to amplifier 100 at the same voltage.

In the context of cardiac stimulation, it is envisioned that square waves of 2 milliseconds or less in duration will generally be applied to the negative input of amplifier 124, to trigger voltage pulses applied to electrode 22. However, ramped voltage waveforms, sinusoidal voltage waveforms or arbitrary voltage waveforms may also be provided to amplifier 124, with corresponding voltage waveforms generated by amplifier 100. Circuitry for generating square voltage pulses, ramped voltage pulses, sinusoidal voltage pulses and/or other arbitrary voltage wave pulses may be employed to define the stimulus current waveform. Such circuitry is believed well known to the art, and is therefore not disclosed in detail herein. For most pacing purposes, it is envisioned that simple rectangular voltage pulses will be applied to VIN line 47, with either pulse amplitude or pulse duration increased in order to increase the energy level of the stimulation pulse applied to electrode 22 by amplifier 100.

As discussed above, following delivery of the stimulation pulse to electrode 22, amplifier 100 delivers current through load resistor 104 to counteract the "polarization" aftereffects associated with delivery of the stimulation pulse (potential present between the electrodes following the application of a stimulation pulse), and to rapidly restore the electrode-tissue system to its previous equilibrium condition. Following delivery of the stimulating pulse, amplifier 100 may quickly (within 10 ms or less) be used for sensing of the occurrence of a depolarization induced by the stimulating pulse and for sensing natural depolarizations of the heart tissue.

Because amplifier 100 is active during delivery of the stimulation pulse, a voltage indicative of the stimulation current will appear at its output. As such, the circuit illustrated provides a ready means of measurement of characteristics associated with the electrode-tissue interface and of the integrity of the pacing lead. The signal indicative of the current delivered to electrode 22, as amplified by amplifier 106 may be passed along to recording and analysis circuitry, if provided, on line 11B. Similarly, because the amplifier 100 is active continually from delivery of the pacing pulse, the current through virtual load resistor 104 immediately following the stimulation pulse to counteract "polarization" after effects may also be passed through amplifier 106 to line 118, for recording and analysis. The current delivered to electrode 22 in the first few milliseconds following delivery of the stimulation pulse may provide information with regard to the condition of the tissue adjacent the electrode 22, or other useful information.

The sensed induced depolarization and natural depolarization wavefronts, of course, also result in corresponding voltage signals at the output of amplifier 100, which may be used for detection of depolarizations using the detection circuitry 116 or may be recorded and analyzed employing any of the waveform analysis techniques known to the art, including measurement of the amplitude, width, slew, etc., of the voltage signal associated with the detected depolarization. This form of analysis is believed to be particularly valuable in conjunction with the use of the present invention in the context of an implantable tachyarrhythmia device, where waveform analysis is likely to be of significance in distinguishing naturally conducted and aberrantly conducted depolarization wavefronts.

Figure 4:
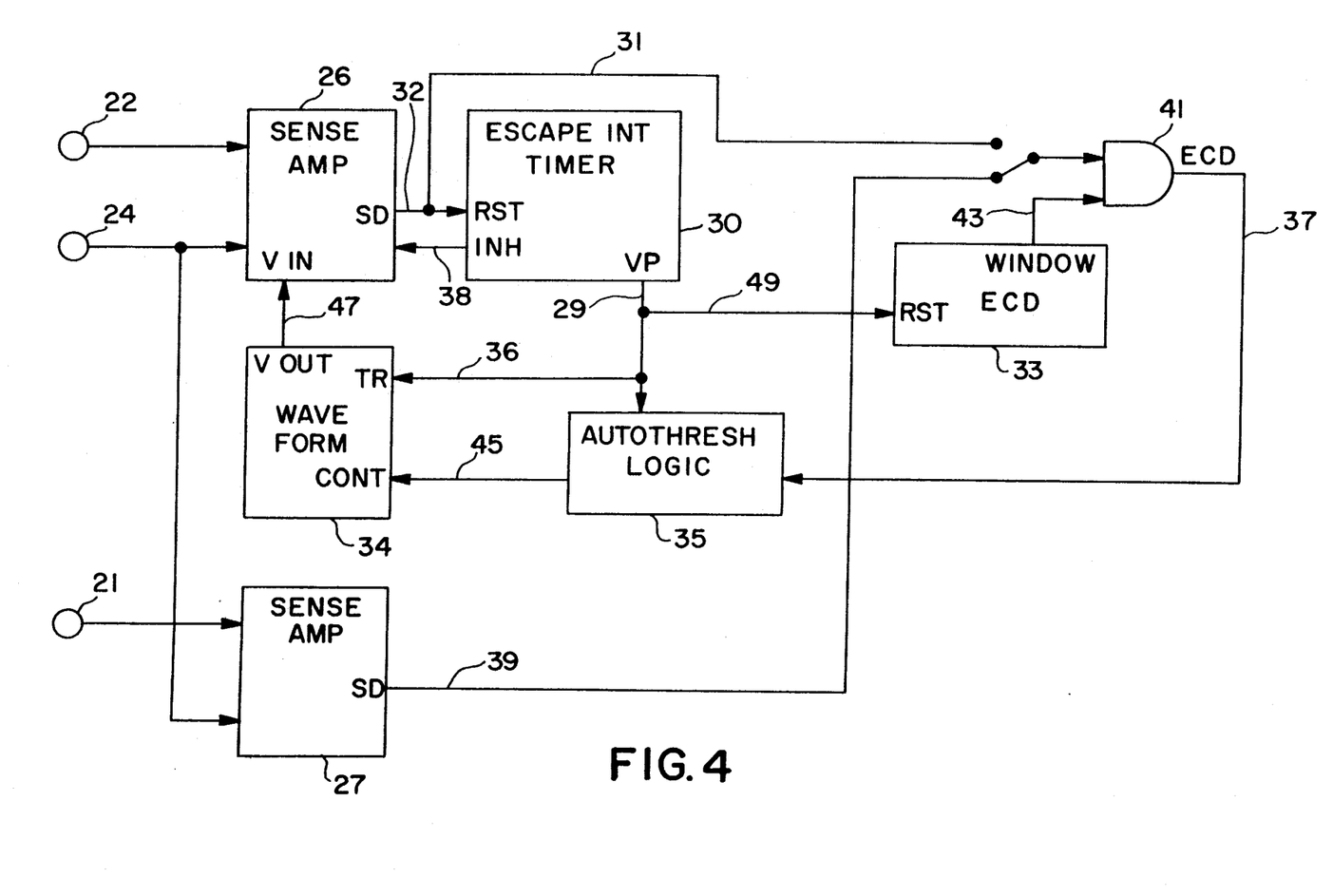
FIG. 4 is a block diagram depicting an auto-threshold cardiac pacemaker employing the circuitry illustrated in FIG. 3.

FIG. 4 depicts the major circuit elements contained within a pacemaker employing the present invention and adapted to detect whether the delivered stimulation pulses are successful in capturing the heart. The sense amplifier 26 is coupled to sense electrical heart signals between the tip electrode 22 and the can electrode 24. The pacing pulse waveform generator 34 is preferably connected to the sense amplifier 26, and serves to define the stimulation pulse waveform as discussed above.

A second field density clamp sense amplifier 27 is also illustrated, coupled to the ring electrode 21 (FIG. 1) and to the pacer can 24. Amplifier 27 may correspond to the sense amplifier illustrated in FIG. 2 and is used to perform the capture detection function as disclosed in the above cited Hudrlik application for a "Electronic Capture Detection for a Pacer".

In operation, the sense amplifier 26 detects the occurrence of a cardiac depolarization, and in response generates a sense detect signal (SD) on line 32. The occurrence of an SD signal resets the escape interval timer 30 and thus resynchronizes the pacer to the underlying rhythm of the patient's heart. If no ventricular depolarizations are sensed within the escape interval, timer 30 generates a ventricular pace signal on line 29 at the expiration of the escape interval. The ventricular pace signal (VP) is provided to the pacing pulse waveform generator circuit 34 via line 36 and triggers generation of a predefined voltage signal as discussed above which controls the current provided to the probe electrode 22. Typically, the escape interval timer 30 is remotely programmed by telemetry to adjust the duration of the ventricular escape interval, which corresponds to the desired maximum time interval between heartbeats.

The VP signal on line 36 generated by the escape interval timer 30 is also communicated to electronic capture detect timer 33 via line 49. The VP signal resets timer 33, which thereafter defines the capture detect time window. During the capture detect window (T2), timer 33 provides a signal on line 43 which enables gate 41. The occurrence of an SD signal from amplifier 26 or amplifier 27 during the capture detect window results in a capture detect signal (ECD) from gate 41 on line 37.

In the case of a typical modern pacemaker, the duration of the pacing pulse may be about 1 ms or less, the amplifier 26 restoring the electrical equilibrium of the electrode/tissue system associated with the probe electrode 22 sufficiently to allow for sensing of tissue depolarization within a few milliseconds thereafter. In embodiments where sense amplifier 27, coupled to the ring and can electrodes is used for capture detection, the capture detect window can begin approximately 10 ms after the ventricular pacing pulse and may end up to 80 to 100 ms thereafter. In embodiments employing amplifier 26 for capture detection, the associated capture detect window would typically have to begin somewhat sooner (e.g. 5-8 ms following delivery of the pacing pulse) to reflect the fact that the induced depolarization waveform as sensed between the tip and can electrodes occurs more closely following the pacing pulse.

Use of amplifier 26 for capture detection purposes is feasible, especially in those cases in which capture is achieved with lower pulse amplitudes so that the amplifier is capable of restoring the equilibrium condition at the electrodes within about 5 ms or less following the pacing pulse. The operation of the pacemaker as illustrated to deliver the lowest energy pacing pulse that reliably effects capture assists in accomplishing this result.

The time interval from the termination of the ventricular pacing pulse to the start of the electronic capture detect window is referred to herein as T1. At the expiration of T1, the capture detect window T2 begins. The T1 period begins at the conclusion of the ventricular pacing pulse. The duration of the T1 period should be short and experimentation suggests that in systems employing field density clamp sense amplifiers, 5-10 ms is an appropriate value. The duration of period T2 should be long enough to allow detection of any pacemaker triggered depolarization. Experimentation suggests that 30-100 ms is an appropriate duration for T2.

Figure 6:
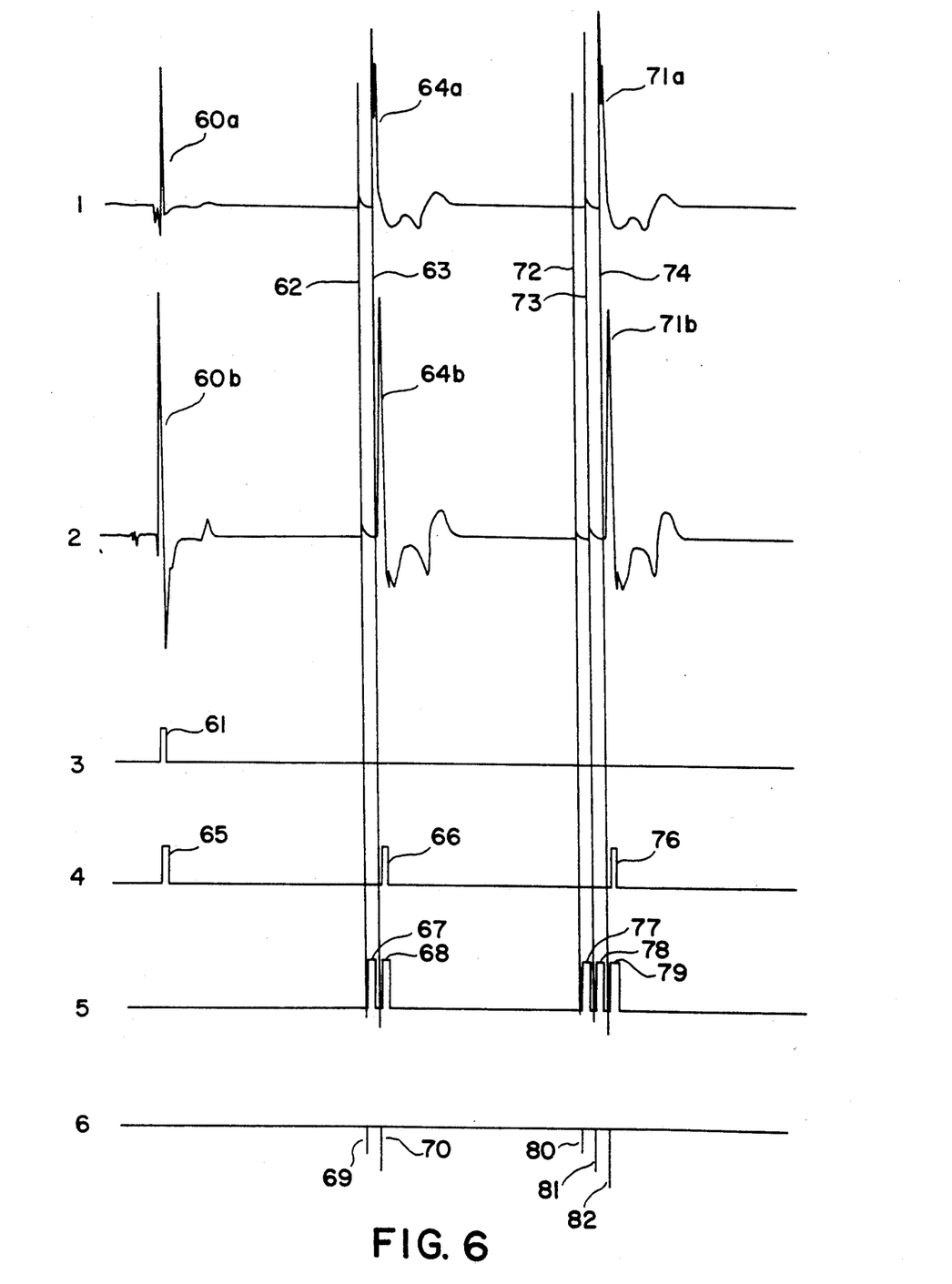
FIG. 6 is a set of real time ECG tracings taken in the laboratory and associated timing diagrams illustrating the operation of the pacemaker illustrated in FIG. 4 in conjunction with detection of depolarizations induced by stimulus pulses.

A capture detect signal (ECD) is generated when the sense amplifier 26 generates an SD signal during the capture detect window T2. This capture detect signal may be used in a variety of ways, and is illustrated in the context of an auto-threshold type pacer. In this instance, the capture detect signal ECD is communicated to auto-threshold logic 35 via line 37. Auto-threshold logic 35 controls the energy content of the pacing pulses delivered by the pulse generator 34 to the lead system. In the event that a pacing pulse is delivered and no capture detect signal follows, auto-threshold logic 35 will generate a control signal on line 45 to increase the amplitude or duration of the voltage signal defined by pacing pulse waveform generator 34, correspondingly increasing the amplitude or duration of the current provided to electrode 22. Auto-threshold logic 35 may also decrement the amplitude or duration of the defined voltage signal in response to an extended period in which all pacing pulses successfully capture the heart to enable a determination of the minimum energy required to reliably pace the heart. Auto-threshold logic 35 may also respond to the failure of a pacing pulse to capture the heart by quickly triggering an additional pacing pulse at an increased energy level, and may continue to trigger increasing energy level pulses until capture is achieved, as illustrated in FIG. 6, below.

Examples of known apparatus for adjusting the energy content of the pacing pulses generated by pulse generator 34 are disclosed in U.S. Pat. No. 4,858,610 issued to Callaghan et al, U.S. Pat. No. 4,878,497 issued to DeCote, all of which are incorporated herein by reference in their entireties. Of course, in the present invention, adjustment will have to be made by varying the defined voltage signals provided to the amplifier 26 rather than by the specific circuitry disclosed in these patents, but the general methodologies disclosed may still be employed.

Alternative pacing functions which may be modified in response to the detection or non-detection of cardiac depolarizations during the capture detect window are described in U.S. Pat. No. 4,795,366 issued to Callaghan et al., and in the above cited U.S. Pat. No. 4,305,396 issued to Wittkampf, both of which are incorporated herein by reference in their entireties.

Figure 5:
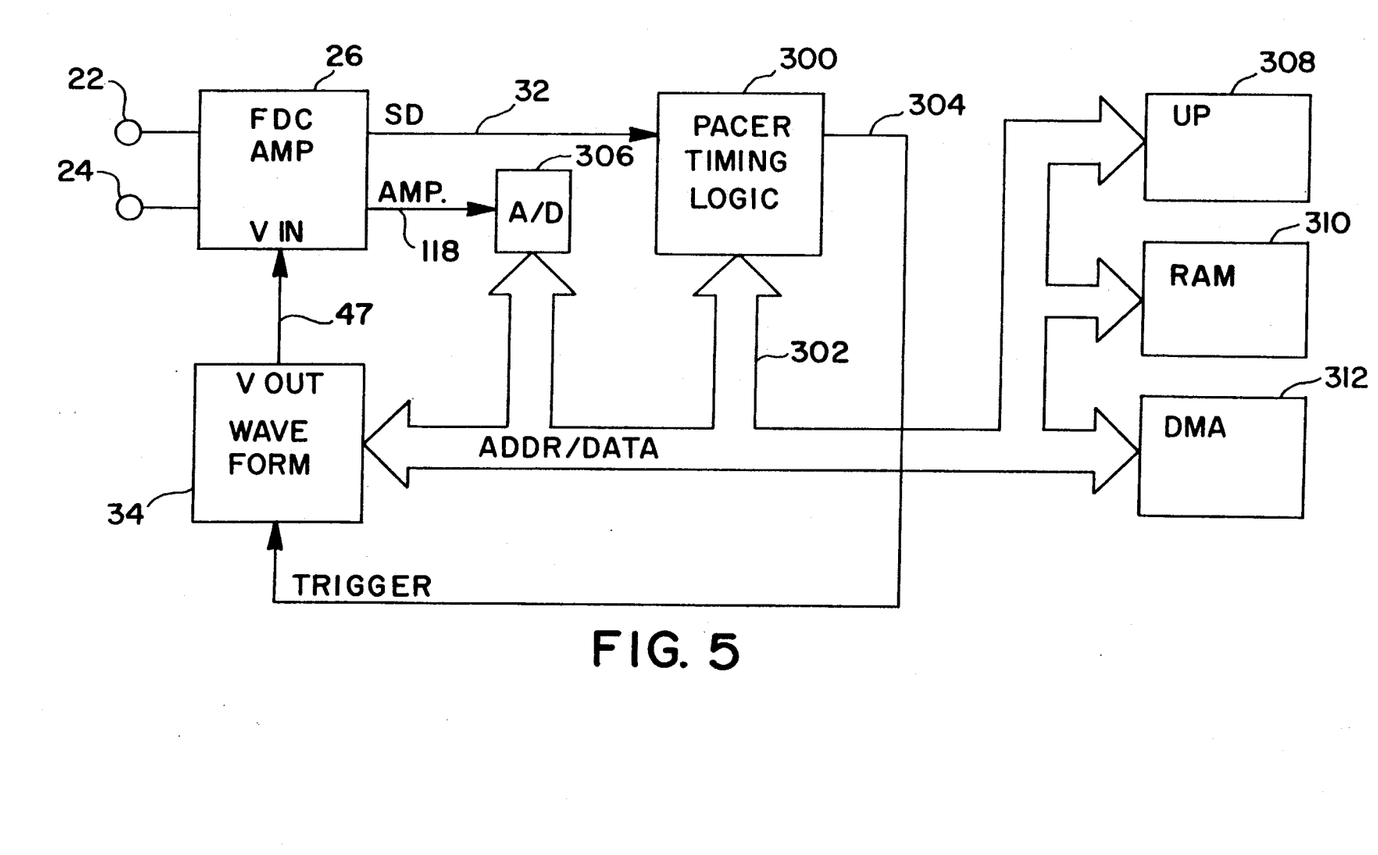
FIG. 5 is a block diagram depicting an alternative embodiment of a cardiac pacemaker employing the circuitry illustrated in FIG. 3.

FIG. 5 is a block diagram of a microprocessor based pacemaker employing the present invention. Operation of the field density clamp amplifier 26 in conjunction with electrodes 22 and 24 and of pacing pulse waveform generator 34 correspond to the operation of the same components discussed above in conjunction with FIGS. 3 and 4. Amplifier 26 provides a sense detect signal on line 32 which is provided to the pacer timing and logic circuitry 300. The analog signal from the operational amplifier within FDC amp 26 is provided on line 118 to an analog to digital converter 306, for storage and waveform analysis.

Pacer timing and logic circuitry 300 includes programmable digital counters and associated logic for controlling the intervals associated with cardiac pacing functions. Most importantly, pacer timing logic 300 includes the escape interval timer, the electronic capture detect window timer and the autothreshold logic illustrated in FIG. 4. The particular intervals timed by pacer timer logic 300 are controlled by microprocessor 308 via address/data bus 302. In response to detection of a depolarization wavefront as indicated by a logic signal on SD line 32, pacer timing logic 300 resets the pacing escape interval timer therein, and initiates any other timing functions that may be desired, under control of microprocessor 308. These may include capture detect windows T1 and T2. On expiration of the ventricular escape interval, a trigger signal is generated on line 4 which triggers pacing pulse waveform generator 34 to deliver a voltage waveform on line 47, as defined by microprocessor 308 via address/data buss 302. For example, in response to the failure of amplifier 26 to detect a depolarization wavefront during electronic capture detect window T2, as communicated to microprocessor 308 via address/data parts 302, microprocessor 308 via address/data parts 302, microprocessor 308 may schedule the immediate delivery of a second pacing pulse at the expiration of interval T2 or shortly thereafter, with an increased amplitude or duration. In response to detection of a sensed contraction during the electronic capture detection window T2, microprocessor 308 may instead instruct pacer timing logic 300 to begin the next subsequent ventricular pacing interval. Similarly, microprocessor 308 may specify occasional gradual reductions in output pulse energy level in order to determine whether the pacing pulses being delivered have an adequate safety margin, as discussed in some of the patents cited above. The analog output from amplifier 26 is provided to an A-D converter 306, which operates under control of microprocessor 308 via address/data bus 302. This structure allows for storage of the output from amplifier 26 during and following generation of stimulus pulses, and in response to detection of spontaneous or induced cardiac depolarizations. For example, a portion of random access memory 310 may be configured as a recirculating buffer, with the digitized output of amplifier 26 stored therein under control of direct memory access circuitry 312. For example, the previous 200 or 300 milliseconds of digitized signal may be present in the recirculating buffer at all times. In response to either delivery of a stimulation pulse or sensing of a depolarization wavefront, microprocessor 308 may freeze the recirculating buffer memory 100 or 200 milliseconds thereafter, and transfer the contents of the buffer to a separate location within memory 310 for later analysis. In this fashion, the waveform of the signal on line 118 corresponding delivered stimulus pulse, the waveform corresponding to the operation of the amplifier 26 to restore the electrode-tissue system to its previous equilibrium state and the induced or spontaneous depolarization waveforms may all be retained for analysis using curve fitting or other forms of digital waveform analysis.

While the embodiment illustrated in FIG. 5 takes the form of a pacemaker, the signal storage and analysis circuitry discussed may equally well be employed in the context of an implantable antitachycardia pacemaker, an implantable cardioverter or an implantable defibrillator, as discussed above, with results of waveform analysis used to distinguish normally conducted and ectopic beats, etc.

The operation of the invention in the context of an auto-threshold pacemaker as discussed above is illustrated in FIG. 6, in tracings 1-6.

Tracing 1 corresponds to the voltage signal at the output of the amplifier 26 on line 118 (FIG. 3), illustrating the pulses delivered to the electrode 22 and R-waves indicative of cardiac depolarization.

Tracing 2 corresponds to the voltage signal at the output of an operational amplifier corresponding to amplifier 38 in FIG. 2, having its inverting input coupled to ring electrode 21 and its non-inverting input coupled to the pacer can 24. Tracing 3 illustrates the logic level output of the sense amplifier 26 (FIG. 5) on line 32 and the pulses illustrated therefore correspond to the SD signals discussed above in conjunction with FIG. 4. Tracing 4 corresponds to the logic level output of amplifier 27 on line 39 (FIG. 4) and similarly indicates the occurrence of sensed ventricular depolarizations.

Tracing 5 corresponds to the signals on line 43 from capture detect timer 33 (FIG. 5). High logic level signals in tracing 4 thus correspond to the durations of the capture detect windows T2 and the spacings between the delivered pacing pulses (62,63,72,73,74) and the T2 windows correspond to the T1 intervals.

Tracing 6 corresponds to the output of the ventricular pacing pulse waveform generator 34 (FIG. 5). The energy level of the pacing pulses delivered is reflected by the height of the pulse markers. The occurrence of pacing pulses is also reflected by the artifacts 62,63,72,73 and 74, which extend across tracings 1-5 and correspond to the output of amplifier 26 (FIG. 4) on 35 during delivery of the pacing pulses.

The first cardiac waveform 60a, 60b results from a normal sinus depolarization of the heart. SD signal 61 on tracing 2 and the SD signal 65 on tracing 4 reflect the detection of this event. In the context of the pacer of FIG. 5, this detected depolarization resets the escape interval timer 30. At the conclusion of the escape interval, timer 30 generates a V-pace signal which triggers a ventricular pacing pulse.

Artifact 62 and pacing pulse marker 69 on tracing 5 indicate the delivery of a pacing pulse. A capture detect window T2 is defined thereafter as indicated at 67, on tracing 5. No depolarization results, as the pacing pulse is of insufficient energy to capture the heart. This lack of capture is evidenced by the fact that no V-sense detect signal on tracing 4 follows the delivery of the pacing pulse at 62. In this instance the auto-threshold logic 35 (FIG. 4) generates another ventricular pacing pulse as indicated by artifact 63. The amplitude of this pacing pulse is increased, as indicated by pacing pulse marker 70 in tracing 6.

In this instance the second pacing pulse captures the heart as evidenced by the depolarization waveform 64a, 64b on tracings 1 and 2. This ventricular depolarization was detected within the capture detect window 68 following the delivery of the pacing pulse at 63, as evidenced by V-sense detect signal 66 in tracing 4. The tracings associated with depolarization waveform 71a, 71b illustrate a sequence of three pacing pulses delivered at 72,73,74. The first two pacing pulses fail to capture the heart, as indicated by the absence of V-sense detect signals thereafter in tracing 4. Pacing pulse energy is increased with each pulse, as indicated by pacing pulse markers 80,81,82. The third pulse delivered at 74 is successful in capturing the heart as indicated by V-sense detect signal 76.

The embodiment of the invention illustrated in FIG. 6 is assumed to employ the sense amplifier 27 to perform capture detection. For this reason, there are no SD signals illustrated on tracing 3 following pacing beats, as the R-wave detector 110 (FIG. 4) is assumed to be inhibited during and shortly following delivery of the pacing pulse. However, if amplifier 26 were to be employed to perform capture detection, SD signals corresponding to those at 66 and 76 would also be illustrated on tracing 3, following pacing pulses 63 and 74, and would correspond to the output of AND gate 41 (FIG. 4).

While the embodiments discussed above all employ field density clamp amplifiers to both sense depolarizations and to deliver stimulus pulses, the field density clamp amplifier may also be used to deliver stimulation pulses in conjunction with prior art type sense amplifiers coupled to the stimulation electrodes. In these circumstances, some blanking of the sense amplifier may be required, however, the ability to deliver voltage pulses of arbitrary waveforms is retained, as well as the ability to return the electrode-tissue system to a state in which depolarizations can rapidly be sensed following stimulus pulses.

In addition, while the embodiments disclosed are ventricular pacemakers, the invention may equally well be practiced in the context of an atrial pacemaker or a dual chamber pacemaker which paces and senses in both the atrium and the ventricle. Similarly, while the pacemakers disclosed in the present application are pacemakers intended to treat bradycardia, the present invention may also be practiced in conjunction with an antitachycardia pacemaker, an implantable cardioverter or an implantable defibrillator. Similarly, the present invention may also be valuable in conjunction with nerve stimulators or muscle stimulators in which delivery of stimulation pulses triggered by sensing of nerve or muscle impulses is desirable or in which arbitrary output waveforms or waveforms which are not readily accomplished by means of a traditional capacitor-type output circuit are desired. Therefore, the scope of the claims that follow should not be construed to be limited to the specific embodiments disclosed herein.

In conjunction with above specification, I claim:

1. A stimulation pulse generator apparatus for a medical electrical stimulator, comprising:
    an operational amplifier having an amplifier output and having first and second amplifier inputs;
    a first electrode electrically coupled to said first input of said amplifier;
    a virtual load electrically coupled between said first electrode and said first input of said amplifier;
    a second electrode coupled to said second input of said amplifier; and
    voltage source means for providing defined pulsatile voltage waveforms to said second input of said amplifier to cause corresponding delivery of voltage pulses to said first electrode.

2. A medical electrical stimulator apparatus, comprising:
    a timing circuit for triggering the generation of stimulation pulses; and
    a pulse generator triggered by said timing circuit to generate stimulation pulses, said pulse generator comprising an operational amplifier having an amplifier output and having first and second amplifier inputs;

a first electrode electrically coupled to said first input of said amplifier;

a virtual load electrically coupled between said first electrode and said first input of said amplifier; second input of said amplifier; and voltage source means for providing defined pulsatile voltage waveforms to said second input of said amplifier to cause corresponding delivery of voltage pulses to said first electrode.

3. A cardiac pacer apparatus, comprising:

a resettable timing circuit for triggering the generation of stimulation pulses;

a pulse generator triggered by said timing circuit to generate stimulation pulses, said pulse generator comprising an operational amplifier having an amplifier output for providing electrical signals and having first and second amplifier inputs;

a first electrode electrically coupled to said first input of said amplifier;

a virtual load electrically coupled between said first electrode and said first input of said amplifier;

a second electrode electrically coupled to said second input of said amplifier; and voltage means for providing defined pulsatile voltage waveforms to said second input of said amplifier to cause corresponding delivery of voltage pulses to said first electrode; and means for detecting a heart depolarization and for resetting said timing circuit in response to detection of a said depolarization, said detecting means responsive to electrical signals provided by said output of said operational amplifier.

4. An apparatus according to claim 3 wherein said detecting means comprises means for defining a capture detection time interval following provision of a said pulsatile voltage waveform to said second input of said operational amplifier and means responsive to detection of a said depolarization occurring during said capture detection time interval for indicating that the said corresponding voltage pulse delivered to said probe electrode was successful in stimulating a heart depolarization.

5. The apparatus of claim 1 or claim 2 or claim 3 or claim 4 wherein said first electrode is adapted for implantation on or in the heart and wherein said first electrode has a surface area of 5 square millimeters or less, and wherein said virtual load has a resistance of 1,000 ohms or less.

6. Apparatus for detecting and stimulating depolarization of cardiac tissue, comprising:

an active circuit having first and second inputs and an output and having means for maintaining said first and second inputs at the same voltage;

a first electrode;

a virtual load coupled between said first electrode and said first input;

a second electrode coupled to said second input; and voltage source means for providing pulsatile voltage signals having defined waveforms to said second input;

wherein said maintaining means comprises means for maintaining said first and second inputs at the same voltage by delivering electrical energy through said virtual load and said first electrode and wherein said output of said active circuit provides a signal indicative of the electrical energy delivered through said virtual load.

7. Apparatus for stimulating tissue, comprising:

an active circuit having first and second inputs and an output and having means for maintaining said first and second inputs at the same voltage;

a first electrode;

a virtual load coupled between said first electrode and said first input;

a second electrode coupled to said second input; and voltage source means for providing pulsatile voltage signals having defined waveforms to said second input;

wherein said maintaining means comprises means for maintaining said first and second inputs at the same voltage by delivering electrical energy through said virtual load and said first electrode, whereby a voltage pulse is delivered to said first electrode in response to the provision of a pulsatile voltage signal by said voltage source means.

8. The apparatus of claim 7 wherein said active circuit comprises monitoring circuitry responsive to the electrical energy delivered through said virtual load and providing said output signal in response to a said delivered energy meeting predetermined criteria.

9. The apparatus of claim 8 wherein said monitoring circuitry comprises means for defining a capture detection time interval following provision of a said pulsatile voltage signal to said second input of said active circuit and means responsive to said output signal occurring during said capture detection time interval for indicating that the said voltage pulse delivered to said probe electrode was successful in stimulating said tissue.

10. The apparatus of claim 6 or claim 7 or claim 8 or claim 9 wherein said first electrode is adapted for implantation on or in the heart.

11. The apparatus of claim 10 wherein said first electrode has a surface area of 5 square millimeters or less, and wherein said virtual load has a resistance of 1,000 ohms or less.

12. The apparatus of claim 6 or claim 7 or claim 8 or claim 9 wherein said active circuit comprises an operational amplifier.

* * * * *

UNITED STATES PATENT AND TRADEMARK OFFICE
CERTIFICATE OF CORRECTION

PATENT NO. : 5,233,985
DATED : August 10, 1993
INVENTOR(S) : Terrence R. Hudrlik It is certified that error appears in the above-indentified patent and that said Letters Patent is hereby corrected as shown below:

Column 2, Line 40, delete "an", and insert in its place --and--.

Column 2, Line 51, after "pacemaker", please insert --as disclosed in the above-cited application Serial No.--.

Column 3, Line 16, delete "foroed", and insert in its place --forced--.

Column 5, Line 46, delete "an", and insert in its place --and--.

Column 5, Lines 63-64, after "reducing the", delete --application--.

Column 6, Line 6, delete "00", and insert in its place --100--.

Column 6, Line 7, delete "00", and insert in its place --100--.

Column 6, Line 68, after "output", delete --5--.

Column 7, Line 45, delete "11B", and insert in its place --118--.

Column 9, Lines 44-45, after "issued" please insert --to Callaghan et al. and U.S. Patent No. 4,729,376 issued--.

Column 10, Line 19, delete "4", and insert in its place --304--.

UNITED STATES PATENT AND TRADEMARK OFFICE
CERTIFICATE OF CORRECTION

PATENT NO. : 5,233,985
DATED : August 10, 1993
INVENTOR(S) : Terrence R. Hudrlik It is certified that error appears in the above-indentified patent and that said Letters Patent is hereby corrected as shown below:

Column 13, Lines 6-7 after "said amplifier;", please insert --a second electrode electrically coupled to said--.

Signed and Sealed this

Fourth Day of October, 1994

Attest:

BRUCE LEHMAN

*Attesting Officer*     Commissioner of Patents and Trademarks